United States Patent [19]

Henderson

[11] Patent Number: 5,364,845
[45] Date of Patent: Nov. 15, 1994

[54] GLUCOSAMINE, CHONDROITIN AND MANGANESE COMPOSITION FOR THE PROTECTION AND REPAIR OF CONNECTIVE TISSUE

[75] Inventor: Robert W. Henderson, Baldwin, Md.

[73] Assignee: Nutramax Laboratories, Inc., Baltimore, Md.

[21] Appl. No.: 40,936

[22] Filed: Mar. 31, 1993

[51] Int. Cl.$^5$ ............... A61K 31/715; A61K 31/70
[52] U.S. Cl. ............................ 514/54; 514/62
[58] Field of Search ............. 514/62, 474, 801

[56] References Cited

U.S. PATENT DOCUMENTS

| | | | |
|---|---|---|---|
| 3,232,836 | 2/1966 | Carlozzi et al. | 167/65 |
| 3,371,012 | 2/1968 | Furuhashi | 167/59 |
| 3,683,076 | 8/1972 | Rovati | 424/180 |
| 3,697,652 | 10/1972 | Rovati et al. | 424/180 |
| 4,006,224 | 2/1977 | Prudden | 424/325 |
| 4,414,202 | 11/1983 | Silvelli | 424/180 |
| 4,486,416 | 12/1984 | Soll et al. | 424/180 |
| 4,647,453 | 3/1987 | Meisner | 424/54 |
| 4,772,591 | 9/1988 | Meisner | 514/62 |
| 4,801,619 | 1/1989 | Lindblad | 514/825 |
| 4,983,580 | 1/1991 | Gibson | 514/2 |
| 5,141,928 | 8/1992 | Goldman | 514/54 |
| 5,162,303 | 11/1992 | Goodman | 514/2 |

OTHER PUBLICATIONS

"Chondroproductive Agents Glucosamine Salts and Chondroitin Sulfates", Luke R . Bucci, Townsend Letters for Doctors, Jan. 1994, pp. 52–54.
Christensen, "Nutritional Support for Three Phases of Rehabilitation" Chiropractic Products, pp. 100–102, Apr. 1993.
Murray, "A Natural Treatment of Osteoarthritis", MPI's Dynamic Chiropractic, pp. 8–10, Sep. 12, 1993.
Morrison, et al., "Cornonary Heart Disease and the Mucopolysaccharides (Glycosaminoglycans)", C. C. Thomas, Publisher, 1974, pp. 109–127.
Drovanti et al, "Therapeutic Activity of Oral Glucosamine Sulfate in Osteoarthrosis; A Placebo–Controlled Double–Blind Investigation", Clin Therap. 3 (4) 260–272 (1980).
Karzel et al, "Effects of Hexosamine Derivatives and Uronic Acid Derivatives on Glycosaminoglycane Metabolism of Fibroblast Cultures", Pharmocol. 5, 337–345 (1971).
"Current Therapy in Equine Medicine", Robinson, Editor, W. B. Saunders Co., Publisher, pp. 402–403 (1987).
Garrison, Jr., et al, "The Nutrition Desk Reference", Keats Publishing, Inc., pp. 70–71 (1985).
Bucci, "Manganese: Its Role in Nurtitional Balance", Today's Chirop., 17 (2) 23–28, 44 (1988).
Bucci, "Glucosamine–A New Potent Nutraceutical For Connective Tissues", The Nutritional Supplement Advisor, Jul. 1992.
Banks, "Applied Veterinary Histology", Williams and Wilkins Publisher, pp. 84–85 (1986).
Setnikar et al, "Pharmakinetics of Glucosamine in the Dog and in Man", Arzneimittelforschung 38 (2) 729–736 (1991).
Vidal y Plana et al, "Articular Cartilage Pharmacology: I. In Vitro Studies on Glucosamine and Non–Steroidal Anti–inflammatory Drugs", Pharm. Res. Comm., 10 (6) 557–569 (1978).
Anon., "Using a Chondroprotective Drug in Treating Dogs With Osteochondrosis", Veterin. Med., 130 (1993).

*Primary Examiner*—Marianne M. Cintins
*Assistant Examiner*—T. J. Criares
*Attorney, Agent, or Firm*—Leonard Bloom

[57] ABSTRACT

A therapeutic composition for the protection, treatment and repair of connective tissue in mammals and a method for the treatment of connective tissue in mammals by the administration of the composition. The composition includes glucosamine and preferably chondroitin sulfate. The composition further includes manganese ascorbate which catalyzes the production of collagen and proteoglycans from the glucosamine and the chondroitin sulfate.

18 Claims, 3 Drawing Sheets

GLUCOSAMINE, CHONDROITIN AND MANGANESE COMPOSITION FOR THE PROTECTION AND REPAIR OF CONNECTIVE TISSUE

FIELD OF THE INVENTION

The present invention relates to therapeutic compositions for the repair of connective tissue in mammals and, in particular to "nutraceutical" compositions capable of promoting chondroprotection, the repair and replacement of mammalian connective tissue.

BACKGROUND OF THE INVENTION

The connective tissues of mammals are constantly subjected to stresses and strains from mechanical forces that can result in afflictions, such as arthritis, joint inflammation and stiffness. Such afflictions are especially acute in joints, such as the neck, back, arms, hips, ankles and feet. Indeed, connective tissue afflictions are quite common, presently affecting millions of Americans. Further, such afflictions cannot only be painful but, in their extreme, can also be debilitory.

The treatment of connective tissue afflictions can be quite problematic. A simple decrease in the stress to which the connective tissue is subjected is often not usually an option, especially in the case of athletes and mammals such as race horses. Thus, an interruption in the traumatic pathways can often not be achieved. Consequently, especially in the case of athletes, humans and animals, treatment is often directed at controlling the symptoms of the afflictions and not their causes, regardless of the stage of the degenerative process.

Presently, steroids, such as corticosteroids, and other anti-inflammatory materials, such as NSAIDS, high doses of aspirin are widely used for the treatment of these ailments; Pharmocol. Res. Commun. 10 557-569 (1978) by Vidal et al. In addition, hyaluronic acid and polysulfated glycosaminoglycan is used in veterinary medicine, especially for equines. While these materials often relieve the pain and swelling associated with maladies arising from connective tissue problems, almost all drugs eventually wear out their effectiveness. Furthermore, drugs may also inhibit the body's own natural healing processes, leading to further deterioration of the connective tissue.

The connective tissues are naturally equipped to repair themselves by manufacturing and remodeling prodigious amounts of collagen (a chief component of connective tissues) and proteoglycans (PG's)—the other major component of connective tissues. This ongoing process is placed under stress when an injury occurs to connective tissues. In such cases, the production of connective tissue (along with collagen and proteoglycans) can double or triple over normal amounts, thereby increasing the demand for the building blocks of both collagens and proteoglycans.

The building blocks for collagen are amino acids, especially proline, glycine and lysine. Proteoglycans (PG's) are large and complex macromolecules comprised mainly of long chains of modified sugars called glycosaminoglycans (GAG's) or mucopolysaccharides. PG's provide the framework for collagen to follow. They also hold water to give the connective tissues (especially cartilage) flexibility, resiliency and resistance to compression.

Like almost every biosynthetic pathway in the body, the pathways by which both collagen and GAG form single molecule precursors, are quite long. As is also characteristic of other biosynthetic pathways, the pathways by which collagen and GAG's are produced include what is called a rate-limiting step—that is, one highly regulated control point beyond which there is a commitment to finish. The presence of such rate-limiting steps permit such complicated processes to be more easily and efficiently controlled by permitting the organism to focus on one point. For example, if conditions demand production and all the requisite raw materials are in place, then stimulation of the rate-limiting step will cause the end product to be produced. To stop or slow production, then the organism needs simply to regulate the rate-limiting step.

In the production of collagen, the rate-limiting step is the maturation, rather than the production, of newly synthesized collagen. Unused collagen is simply degraded back to amino acids. Proteoglycans, however, have a specific rate-limiting step in their production.

In the production of PG's, the rate-limiting step is the conversion of glucose to glucosamine for the production of GAG's. Glucosamine is the key precursor to all the various modified sugars found in GAG's—glucosamine sulfate, galactosamine, N-acetylglucosamine, etc. Glucosamine also makes up 50% of hyaluronic acid—the backbone of PG's—on which other GAG's, like chondroitin sulfates are added. The GAG's are then used to build PG's and, eventually, connective tissue. Once glucosamine is formed, there is no turning away from, the synthesis of GAG polymers and the synthesis of collagen.

There are several disclosures of which we are aware wherein it has been suggested to bypass the rate-limiting step of the conversion of glucose to glucosamine in those pathways that produce proteoglycans by the provision of exogenous quantities of glucosamine. For example, the intravenous administration of glucosamine (a precursor of the GAG's) and derivations thereof have been disclosed in U.S. Pat. No. 3,232,836 issued to Carlozzi et al, for assisting in the healing of wounds on the surface of the body. In U.S. Pat. No. 3,682,076 issued to Rovati, the use of glucosamine and salts thereof are disclosed for the treatment of arthritic conditions. Finally, the use of glucosamine salts has also been disclosed for the treatment of inflammatory diseases of the gastrointestinal tract in U.S. Pat. No. 4,006,224 issued to Prudden.

There have also been several disclosures of which we are aware wherein it has been suggested to go one step further in bypassing the rate-limiting step, by providing excess quantities of various of the modified sugars found in the GAG's for producing proteoglycans. For example, in U.S. Pat. No. 3,6797,652 issued to Rovati et al, the use of N-acetylglucosamine is disclosed for treating degenerative afflictions of the joints.

In still other disclosures of which we are aware, it has been taught to go still one step further in bypassing the glucose to glucosamine rate-limiting step by providing excess quantities of the GAG's themselves (with and without various of the modified sugars). For example, in U.S. Pat. No. 3,371,012 issued to Furuhashi, a preservative is disclosed for eye graft material that includes galactose, N-acetylglucosamine (a modified sugar found in the GAG's) and chondroitin sulfate (a GAG). Additionally, U.S. Pat. No. 4,486,416 issued to Soll et al, discloses a method of protecting corneal endothelial cells exposed to the trauma of intraocular lens implantation surgery by administering a prophylactically effective amount of chondroitin sulfate. Also, U.S. Pat. No. 5,141,928 issued to Goldman discloses the prevention and treatment of eye injuries using glycosaminoglycan polysulfates.

U.S. Pat. No. 4,983,580 issued to Gibson, discloses methods for enhancing healing of corneal incisions. These methods include the application of a corneal motor composition of fibronectin, chondroitin sulfate and collagen to the incision.

Finally, in U.S. Pat. No. 4,801,619 issued to Lindblad, the intraarticular administration of hyaluronic acid is disclosed for the treatment of progressive cartilage degeneration caused by proteoglycan degradation.

While the above references have, to varying degrees, been useful for their intended purposes, none have proven entirely satisfactory. In particular, the absorption rates of the various compositions disclosed have not been entirely satisfactory nor have their ability to increase GAG production. In addition, none of the compositions are provided with both the glucosamine starting material in conjunction with a GAG (such as chondroitin sulfate). Finally, none of the disclosured compositions include any catalysts which facilitate the production of PG's from its various building blocks.

Accordingly, it can be seen that there remains a need for a therapeutic composition which include glucosamine, GAG's and catalysts for aiding in the conversion of these materials to protoglycans for facilitating the repair of connective tissue in mammals.

SUMMARY OF THE INVENTION

It is a primary object of the present invention to provide a therapeutic composition for the protection and repair of connective tissue in mammals.

It is a further primary object of the present invention to provide such a therapeutic composition which is a nutraceutical—that is, a composition which includes only naturally-occurring components capable of providing beneficial therapeutic effects.

It is a further primary object of the present invention to provide such a nutraceutical which contains glucosamine and which further contains GAG's and catalysts capable of aiding in the conversion of these materials to PG's for facilitating the repair of connective tissue in mammals.

It is a further primary object of the present invention to provide such a nutraceutical composition which exhibits increased absorption rates.

In accordance with the teachings of the present invention, disclosed herein is a therapeutic composition capable of the protection, treating and repairing of connective tissue in mammals. The composition includes glucosamine and salts thereof, such as glucosamine hydrochloride and glucosamine sulfate, which stimulate both collagen and proteoglycan synthesis. The composition preferably includes chondroitin sulfate. Finally, the composition includes manganese ascorbate which acts as a catalyst in absorption and in the production of both proteoglycans and collagens.

The provision of manganese ascorbate along with chondroitin sulfate in the composition of the present invention provides synergistic effects in that the manganese acts as a cofactor for catalyzing the conversion of the glucosamine into hyaluronic acid. The manganese further acts as a cofactor which, in combination with the sulfate ($SO_4$), provides synergistic effects in converting the glucosamine into GAG's necessary for cartilage.

In further accordance with the teachings of the present invention, disclosed herein is a method for the protection, treatment and repairing of connective tissue in mammals. This method includes the administering of therapeutically effective amounts of glucosamine, including salts thereof, in the presence manganese and preferably, chondroitin sulfate for stimulating both collagen and proteoglycan synthesis.

These and other objects of the present invention will become readily apparent from a reading of the following description, when taken in conjunction with the enclosed drawing.

DESCRIPTION OF PREFERRED EMBODIMENTS

The composition of the present invention includes glucosamine (in a salt form), a manganese salt, preferably ascorbate and preferably chondroitin sulfate. According to the principles of the present invention, a composition of glucosamine and chondroitin sulfate, in exogenous quantities, and in combination with manganese ascorbate are provided to a mammal in need thereof. Manganese ascorbate is preferred because it is a soluble salt which also provides ascorbic acid needed for collagen synthesis, but other manganese salts such, as for example, sulfate or gluconate, may be used but not preferred. In this fashion, the glucose to glucosamine rate-limiting step in the mammal's natural production of collagen and proteoglycans will be bypassed, for production of additional quantities of collagen and proteoglycans, so as to be available for use by the mammal's natural healing processes to repair connective tissue.

The glucosamine is the base of the composition, providing the primary substrate for both collagen and proteoglycan synthesis. In fact, glucosamine is the preferred substrate for proteoglycan synthesis, including chondroitin sulfates and hyaluronic acid. The glucosamine is, preferably, in a salt form so as to facilitate its delivery and uptake by the mammal. The preferred salt forms are glucosamine hydrochloride and glucosamine sulfate. It is noted here that, in the case of the glucosamine sulfate, the sulfate may be available for later use in catalyzing the conversion of glucosamine to GAGs. The unsulfated form is desired for the production of hyaluronic acid.

Glucosamine has been shown to be rapidly and almost completely absorbed into humans and animals after oral administration. A significant portion of the ingested glucosamine localizes to cartilage and joint tissues, where it remains for long time periods. This indicates that oral administration of glucosamine reaches connective tissues, where glucosamine is incorporated into newly-synthesized connective tissue.

In vitro, glucosamine has demonstrated increased synthesis of collagen and glycosaminoglycans from fibroblasts which is the first step in repair of connective tissues. In vivo, topical application of glucosamine has enhanced wound healing. Glucosamine has also exhibited reproducible improvement in symptoms and cartilage integrity in humans with osteoarthritis in a series of studies. (Nutritional Supplement Advisor, July 1992 by Bucci)

Figure 1:
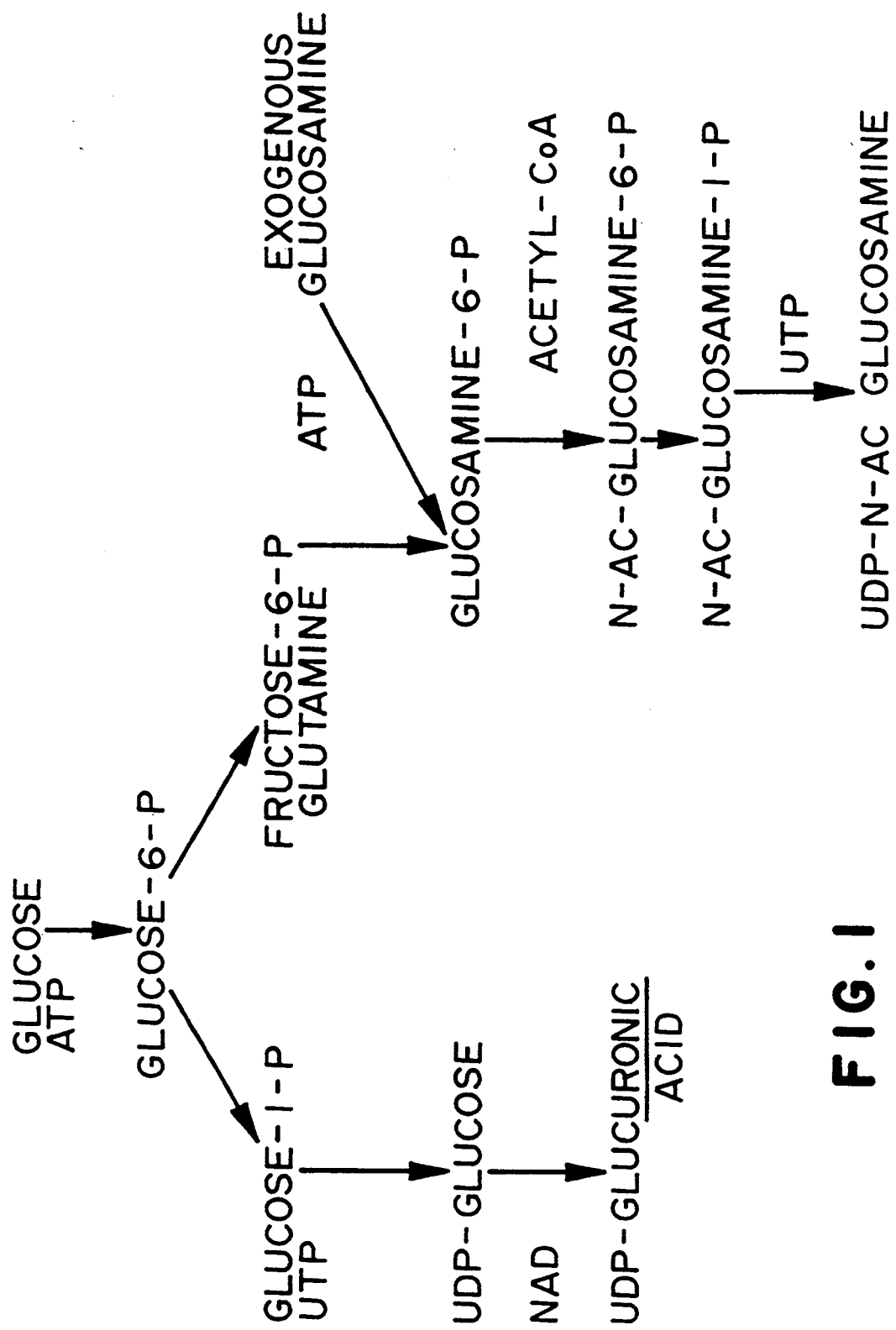
FIG. 1 is a sequence for the biosynthesis of hexosamines.

One of the monosaccharides in the disaccharides unit is an aminosugar, either glucosamine or galactosamine. The other monosaccharide is either uronic acid or galactose. The repeating units contain one (1) hexosamine thus showing the importance of glucosamine which increases the biosynthesis of hexosamines as shown in the sequence of FIG. 1. The glucosamine is provided from the composition of the present invention. All GAG's contain hexosamine or uronic acid derivative products of the glucose pathway and from exogensis glucosamine as for example:

| | |
|---|---|
| Hyaluronic Acid | Glucosamine + Glucuronic Acid |
| Keratan-Sulfate | Glucosamine + Galactose |
| Chondroitin Sulfate | Glucuronic Acid + Galactosamine |
| Heparin Sulfate | Glucosamine + Glucuronic or Iduronic Acid |
| Dermatin Sulfate | Iduronic Acid + Galactosamine |

Chondroitin sulfate is a GAG that provides a further substrate for the synthesis of the proteoglycans. Once again, the provision of the chondroitin in its salt, sulfate form, facilitates its delivery and update by the mammal. Also, the sulfate is once again available for further use in catalyzing the conversion of the chondroitin sulfate into proteoglycans.

Chondroitin sulfate not only provides additional organic sulfur to the formula for incorporation into cartilage but it also has a synergistic effect with glucosamine since its structure provides galactosamine which is a different pathway than that used by glucosamine (Pharmacology 5 337-345 (1971) by Karzel et al) (see FIG. 1). The hexosamine and uronic acid pathway is the primary pathway for mucopolysaccharides (GAG) production. Glucosamine is, by far, the more active ingredient.

In addition chondroitin sulfate has been shown to have cardiovascular health benefits [Coronary Heart Disease and the Mucopolysaccharides (Glycosaminoglycans) (1973) pp. 109-127 by Morrison et al]. Thus, it is preferred that chondroitin sulfate be present.

Manganese, an important synergist to the composition, plays a central role in the synthesis of GAGS, collagen and glycoproteins which are important constituents of cartilage and bone. Manganese is required for enzyme activity of glycosyltransferases. This family of enzymes is responsible for linking sugars together into glycosaminoglycans, adding sugars to other glycoproteins, adding sulfate to aminosugars, converting sugars into other modified sugars, and adding sugars to lipids. These functions are manifested as glycosaminoglycan synthesis (hyaluronic acid, chondroitin sulfate, keratan sulfate, heparin sulfate and dermatin sulfate etc.), collagen synthesis, and function of many other glycoproteins and glycolipids. Glycosaminoglycans and collagen are the chief structural elements of all connective tissues. Their synthesis is essential for proper maintenance and repair of connective tissues.

Manganese deficiencies in animals leads to abnormal bone growth, swollen and enlarged joints, and slipped tendons. In humans, manganese deficiencies are associated with bone loss and arthritis. Levels of all glycosaminoglycans are decreased in connective tissues during manganese deficiencies, with chondroitin sulfates being most depleted. Manganese-deficient organisms quickly normalize glycosaminoglycans and collagen synthesis when manganese is repleted.

Manganese is also required for activity of manganese superoxide dismutase (MnSOD), which is present only in mitochondria. Manganese deficiency decreases the activity of MnSOD and may lead to mitochondrial dysfunction, manifested as decreased cellular functions.

Approximately 40% of dietary manganese is absorbed by the body tissue storage minimal with a mere 12 to 20 mg present in the body at any one time. Large amounts of calcium and phosphorus in the intestine are known to interfere with absorption. The richest dietary sources are the foods least consumed by the general public as whole grain cereals and breads, dried peas, beans and nuts. The ascorbate form of manganese is preferred due to the high bioavailability and the need for vitamin C (ascorbic acid) for collagen production. Vitamin C also enhances manganese uptake by the body. However, other soluble forms of manganese may be used but with lesser value.

Manganese plays a central role in the synthesis of glycosaminoglycans and glycoproteins, which are important constituents of cartilage and bone. Many reproductive problems in horses and skeletal abnormalities in foals have been ascribed to manganese deficiency. [Current Therapy in Equine Medicine, 2 (1987), pp. 402-403.]

In the present method for the treatment and reparation of connective tissue in mammals, therapeutic amounts of excess quantities of glucosamine including salts thereof in the presence manganese and preferably, also with chondroitin sulfate, are administered to mammals in need thereof for stimulating both collagen and proteoglycan synthesis.

Figure 2:
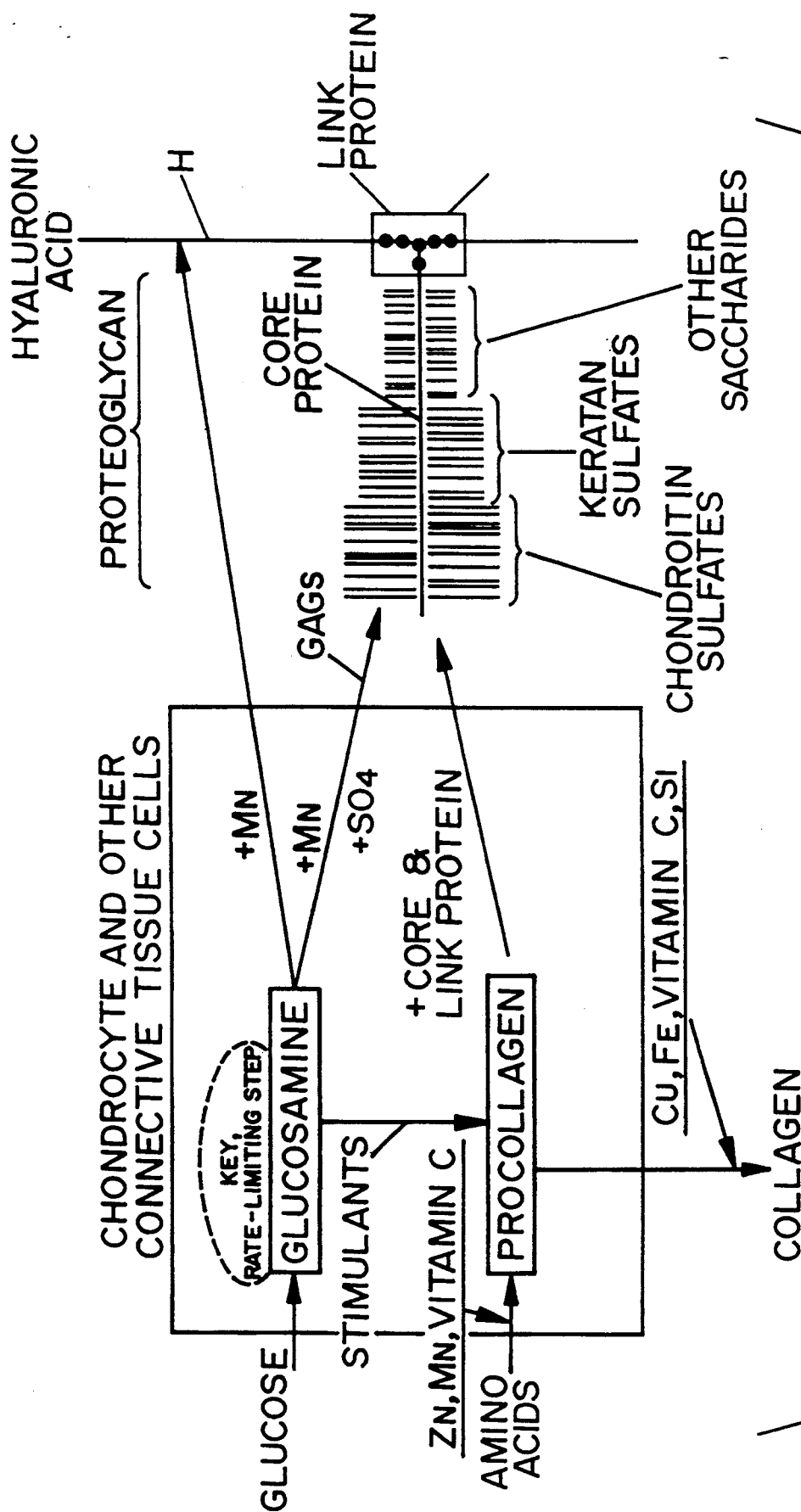
FIG. 2 is a schematic flowchart illustrating the biological pathway by which the composition of the present invention aids in protection and repair of connective tissue.
Figure 3:
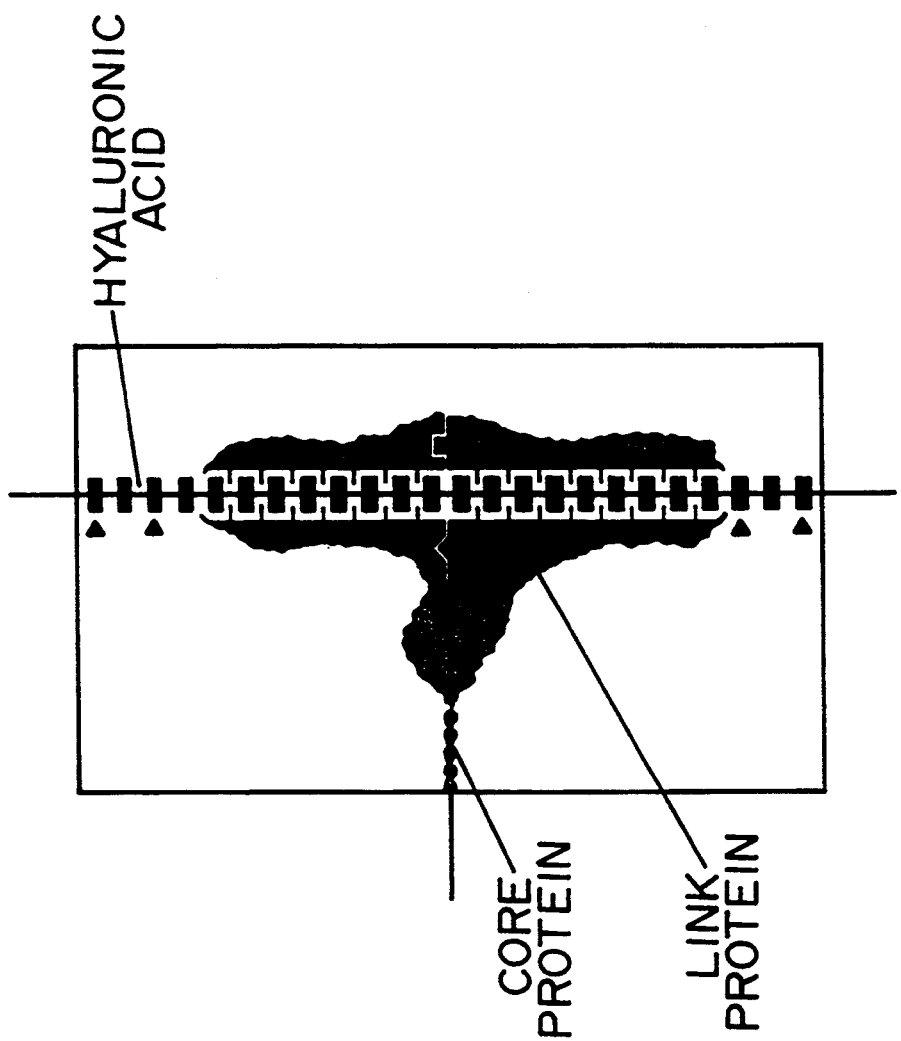
FIG. 3 is an enlarged portion of the flowchart of FIG. 2.

Referring to FIGS. 2 and 3, the biosynthetic pathway is now discussed by which the method of the present invention, by virtue of the components of the composition of the present invention, aids in the connective tissue repair of mammals.

Administration of the composition of the present invention provides the mammalian organism with exogenous quantities of glucosamine and chondroitin sulfate. The composition also provides the mammalian organism with exogenous quantities of manganese cofactors and sulfates.

The exogenous glucosamine provided by the composition of the present invention is converted to both proteoglycans and collagen, as is seen in FIG. 2.

In the former case, the glucosamine may be converted with the aid of a manganese cofactor directly into hyaluronic acid (which is 50% glucosamine and which forms the backbone of the PG's). Also, the glucosamine may, with the aid of the manganese cofactors and the sulfates available, be converted into GAG's. These GAG's are then converted into chondroitin sulfate which form a part of the core protein, as is seen in FIG. 2. This core protein is then linked to the hyaluronic acid via the link protein, as is seen in FIG. 3.

In the latter case, the glucosamine is, with the aid of stimulants, converted into procollagen. Similarly, the free amino acids are, with the aid of the zinc, manganese cofactors (and ascorbic acid or vitamin C chelates), converted to procollagen. The procollagen is then converted into collagen with the aid of copper or iron cofactors and vitamin C (ascorbic acid) and sulfate chelates.

The efficacy of the composition of the present invention has been demonstrated. In vitro cultures of cartilage and connective tissue cells that were provided with the composition of the present invention produced more hyaluronic acid, more chondroitin sulfate, more collagen and more matrix than controls or other GAG precursors. While glucosamine increased GAG production by 170% in cultured connective tissue cells, other modified sugars or GAG components were ineffective.

Furthermore, administration of the glucosamine in the composition of the present invention to human cartilage explants improved biomechanical properties. Physiological (low) doses increased cartilage synthesis in animals by 10% which is quite large in real life.

Glucosamine is naturally-occurring in connecting tissue and can be considered a nutrient when ingested in foods. Although usually as part of connective tissue, glucosamine is a normal body component that happens to be an important control element and raw material. It is a nutraceutical—a nutrient with clinical usefulness.

Furthermore, being a small, naturally-occurring molecule, glucosamine is almost completely absorbed when given orally (greater than 95%), as shown by animal and human studies. Even more important, 30% of an oral dose is retained by the musculoskeletal system for long time periods. Daily oral dosing was found to raise tissue levels of glucosamine better than intravenous administration. Glucosamine is non-toxic, with oral doses of 8 grams per Kg body weight to mice, rats, rabbits and dogs not causing any problems, even after months of dosing. (The Nutritional Supplement Advisor, July 1992, by Bucci).

Thus, it can be seen that the composition of the present invention containing glucosamine, purified chondroitin sulfates and manganese ascorbate, advantageously stimulates the synthesis of collagen and glycosaminoglycans or mucopolysaccharides (GAG's), including hyaluronic acid, the backbone of proteoglycans (PG's), thereby providing a natural tissue repair function. This composition provides the superior connective tissue repair function of glucosamine, plus synergistic benefits from chondroitin sulfates and manganese. The tissue repair can be in the context of cartilage repair and the treatment of arthritic conditions as well as connective tissue damage in most all areas of the body both human and animal.

Having discussed the composition of the present invention, it will be more clearly perceived and better understood from the following specific examples.

The composition of the present invention is made in a capsule form for oral administration to humans and small mammals in need thereof. Each capsule contains:

| Human & Small Animal | Tabs, Capsules | Range/Dose |
| --- | --- | --- |
| Glucosamine | 250 mg | 250–750 mg |
| Chondroitin Sulfate | 200 mg | 50–200 mg |
| Manganese (as Ascorbate) | 5 mg | 2–25 mg |
| Ascorbate (as Manganese Ascorbate) | 33 mg | 13–165 mg |

Dosages of 1–6 capsules (or as otherwise needed) are administered daily to the mammal in need thereof to effectuate connective tissue protection and repair.

For larger mammals such as horses, the composition is administered as filled scoops.

| Large Animal (Equine) | Level Scoopful | Range/Dose |
| --- | --- | --- |
| Glucosamine | 1800 mg | 1000–3000 mg |
| Chondroitin Sulfate | 600 mg | 250–1000 mg |
| Manganese (as Ascorbate) | 16 mg | 10–125 mg |
| Ascorbate (as Manganese Ascorbate) | 104 mg | 65–825 mg |

The composition may omit the chondroitin sulfate if desired, although a more effective composition is obtained which includes the chondroitin sulfate.

The following case studies were conducted with mammals. The unexpected speed of response of animal recovery demonstrate the effectiveness of the treatment.

Case #1

Five month old female intact Rottweiler, presented with chief complaint of difficulty getting up in the rear and occasional crying in pain when walking. Physical exam revealed pain on palpation of hips with crepitation in right hip. Preliminary diagnosis was hip dysplasia. Radiographs diagnosed bilateral hip dysplasia with approximately ¼ of femoral head seated in the acetabulum. The owners were contemplating euthanasia. The dog was placed on three (3) capsules of the present invention two times daily for two weeks. At two week recheck, the dog was moving better and getting up easier. At one month, the dog was running, climbing stairs, and the owners were amazed. The animal is presently doing well and is still on a maintenance dose of two (2) capsules two times daily.

Case #2

A nine year old intact pure breed certified Rottweiler presented with difficulty rising in rear and a wobbly gait in the hind quarters. Physical exam revealed pain on manipulation of hips. A preliminary diagnosis of degenerated joint disease (DJD) was made. The dog was placed on three (3) capsules of the present invention two times daily for one month and re-evaluated at two weeks and one month. At two weeks, the dog was rising better, and the gait was almost normal at one month. The dog was 65% improved according to the breeder and improving weekly. The dog is currently on a maintenance dose of two (2) capsules two times daily.

Case #3

A 12 year old neutered Collie presented with generalized muscle weakness and inability to rise in rear without assistance. The Collie could only walk about 10 feet before it would collapse from muscle weakness. The owners were contemplating euthanasia. Physical exam revealed atrophy of hind leg musculature and pain on deep palpitation of hips. Mild proprioceptive deficits in rear were also noted on neurological exam. X-rays revealed moderate DJD of hips but was not deemed severe enough to explain all of the symptoms. A preliminary diagnosis of degenerative myopathy with 2nd degree DJD was made. The Collie was placed on Prednisone for two (2) weeks with mild improvement. On recheck, the Collie was placed on three (3) capsules of the present invention for one month as well as continuation of the Prednisone. At two (2) week recheck, the dog has improved moderately and was able to get up and down on its own. The Prednisone was discontinued and the dog was kept on the capsule of the present invention. At one (1) month recheck, the dog was 50% improved and able to get up and down without assistance and walk around the yard without a wobbly gait. At three (3) months recheck, the dog was significantly improved—walking normally around the yard and going up and down the stairs. The dog is on two (2) capsules two times daily as a maintenance dose. Earlier the dosage was decreased to one (1) capsule two times daily but after one week, the owner noticed an uneasiness in the gait.

Case #4

A 4 year old spayed Dachshund presented with acute yelping in pain when jumping up on a chair. The dog then went off of food and whimpered when picked up. Physical exams revealed pain in lumbar vertebrae. X-rays revealed inter vertebral disk disease at L2–L3 and mild proprioceptive deficits in rear legs were noted. The dog was placed on Prednisone and rest for 2 weeks. At the 2 week check, the dog was clinically normal with mild discomfort on deep palpitation of lumbar vertebrae. The dog was placed on 1 capsule of the present invention, two times daily as a preventative and to strengthen connective tissue of adjacent disk spaces. No further disk disease has taken place.

Case #5

A 1 year old Doberman Pinscher presented with pain on getting up. X-rays were taken and revealed severe dysplasia with osteophyte formation. The dog was placed on three (3) capsules of the present invention, three times daily, for 2 weeks. At 2 week checkup, the dog was in much less pain and is currently doing well on 2 capsules two times daily, maintenance dose.

Case #6

A nine year old cat presented with a limp in the right rear leg. Pain was noticed on extension of the stifle joint. Radiographs revealed severe DJD in the stifle joint. The cat was placed on one (1) capsule of the present invention, two times daily for one month. At one month recheck, the cat had a mild limp but no pain in the joint. The cat is currently on one (1) capsule four (4) times daily and doing well. The owners reported that they stopped administration of the present invention for one (1) week and the pain returned.

Case #7

A nine year old Doberman Pinscher presented with extreme difficulty rising in the rear, inability to go up and down stairs, and a wobbly gait in the hind quarters. The owners believed the dog to be in constant pain. Myelogram by veterinarian diagnosed cervical vertebral instability with slipped discs at C 5-6, C 6-7. The veterinarian prescribed Prednisone and rest for three weeks and gave prognosis as poor for recovery. The owners said the dog seemed to improve while on Prednisone but symptoms returned when Prednisone was stopped. The dog was placed on three (3) capsules of the present invention, two times daily. At two week recheck, the dog was moving better and getting up easier. At six weeks, the dog was running. At six months, physical exam revealed no pain on manipulation of neck and hips. The dog is currently on three (3) capsules two times daily and doing well.

Case #8

The thoroughbred race horse had a history of chips in ankle. In 1990, the Cornell University Veterinary School worked on the horse. X-rays showed an undiagnosed spot on the ankle. More recent x-rays showed injured sesamoid and joint damage. By 1992, the horse was very lame. The knee was carrying heat and there was little strength in the hock and stifle. The sacroiliac was arthritic and vertebrae slumped so severely that the horse could barely support a rider. The horse rebelled at the track and could not change leads. As a result, the horse was placed on veterinarian list at the track. Use of the powder of the present invention was initiated. The dosage was two (2) scoops two times daily. Within 5 days, the back problem improved to where a rider could be supported and the horse's posture was markedly improved. After 30 days, the horse no longer rebelled upon entering track. The stifle and hock improved in strength and the knee was cold. After 8 weeks, the stifle and hock were tight, and the back was strong. The horse is running two miles without discomfort and will race as soon as track conditions improve. The horse is currently on a maintenance dose of one (1) scoop of the present invention, two times daily increasing to two (2) scoops two times daily during workouts.

Case #9

The thoroughbred race horse was diagnosed with osteoarthritis in the knee and shoulder. The horse was considered lame with very little movement in the shoulder and knee. The knee was carrying heat. Use of the powder of the present invention was initiated at a dosage of three (3) scoops two times daily. After 15 days, the horse showed improved movement in the shoulder. At 25 days, the heat was gone from the knee and movement of the horse was markedly improved. The horse is scheduled to begin training approximately six weeks after initiation of treatment with the composition of the present invention.

These cases demonstrate the efficacy of the composition of the present invention when compared to other treatments. The actions of the animals after treatment is testimony to the improvement in the conditions of the disorder from which the animal suffered prior to treatment with the composition of the present invention. Similar results have been seen with treated humans, but animal cases do not need double blind studies. The effect cannot be a placebo, since the animals did not know they were being treated.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. A therapeutic composition for the treatment and repair of connective tissue in mammals, comprising: therapeutic quantities of glucosamine and salts thereof, in combination with chondroitin sulfate and soluble salts of manganese, for stimulating production of proteoglycans and collagens in mammals in need thereof for treatment and repairing the connective tissue.

2. The therapeutic composition of claim 1, wherein the glucosamine is glucosamine hydrochloride.

3. The therapeutic composition of claim 1, wherein the glucosamine is glucosamine sulfate.

4. The therapeutic composition of claim 1, wherein a dose of the glucosamine ranges from 250 mg to 3000 mg.

5. The therapeutic composition of claim 4, wherein the dose for humans and small mammals is approximately 250 mg.

6. The therapeutic composition of claim 4, wherein the dose of glucosamine for horses and large mammals is approximately 1800 mg.

7. The therapeutic composition of claim 1, wherein a dose of chondroitin sulfate ranges from 50 mg to 1000 mg.

8. The therapeutic composition of claim 7, wherein the dose of chondroitin sulfate for humans and small mammals is approximately 200 mg.

9. The therapeutic composition of claim 7, wherein the dose of chondroitin sulfate for horses and large mammals is approximately 600 mg.

10. The therapeutic composition of claim 1, wherein the soluble manganese salt is manganese ascorbate.

11. The therapeutic composition of claim 10, wherein the dose of manganese ascorbate ranges from 75 mg to 950 mg.

12. The therapeutic composition of claim 11, wherein the dose of manganese ascorbate for horses and large mammals is approximately 120 mg.

13. The therapeutic composition of claim 1, wherein the dose of glucosamine ranges from 250 mg to 3000 mg, the dose of chondroitin sulfate ranges from 50 mg to 1000 mg, the manganese salt is manganese ascorbate and the dose of manganese ascorbate ranges from 15 mg to 950 mg.

14. The therapeutic composition of claim 10, wherein the dose of manganese ascorbate for humans and small mammals is approximately 38 mg.

15. The therapeutic composition of claim 13, wherein the dose for humans and small mammals is approximately 250 mg of glucosamine, approximately 200 mg of chondroitin sulfate and approximately 38 mg of manganese ascorbate.

16. The therapeutic composition of claim 13, wherein the dose for horses and large mammals is approximately 1800 mg of glucosamine, approximately 600 mg of chondroitin sulfate and approximately 120 mg of manganese ascorbate.

17. A method for the, treatment and reparation of connective tissue in mammals, comprising the steps of administering a therapeutically effective quantity of glucosamine, including salts thereof, chondroitin sulfate and a soluble manganese salt to a mammal in need thereof, whereby the mammal's natural production of collagen and proteoglycans is increased for treating and repairing the connective tissue of the mammal.

18. A method for the treatment and reparation of connective tissue in mammals, comprising the steps of orally administering a therapeutically effective quantity of glucosamine, including salts thereof, chondroitin sulfate and a soluble manganese salt to a mammal in need thereof, whereby the mammal's natural production of collagen and proteoglycans is increased for treating and repairing the connective tissue of the mammal.

* * * * *

UNITED STATES PATENT AND TRADEMARK OFFICE
CERTIFICATE OF CORRECTION

PATENT NO. : 5,364,845
DATED : November 15, 1994
INVENTOR(S) : Robert W. Henderson It is certified that error appears in the above-indentified patent and that said Letters Patent is hereby corrected as shown below:

In claim 11, column 11, line 14, "75" should read —15—.

Signed and Sealed this

Third Day of September, 1996

Attest:

BRUCE LEHMAN

Attesting Officer      Commissioner of Patents and Trademarks

REEXAMINATION CERTIFICATE (4639th)

United States Patent
Henderson

(10) Number: US 5,364,845 C1
(45) Certificate Issued: Sep. 10, 2002

(54) GLUSOSAMINE, CHONDROITIN AND MANGANESE COMPOSITION FOR THE PROTECTION AND REPAIR OF CONNECTIVE TISSUE

(75) Inventor: Robert W. Henderson, Baldwin, MD (US)

(73) Assignee: Nutramax Laboratories, Inc., Baltimore, MD (US)

Reexamination Request:
No. 90/005,599, Dec. 24, 1999

Reexamination Certificate for:
Patent No.: 5,364,845
Issued: Nov. 15, 1994
Appl. No.: 08/040,936
Filed: Mar. 31, 1993

Certificate of Correction issued Sep. 3, 1996.

(51) Int. Cl.$^7$ ........................ A61K 31/715; A61K 31/70
(52) U.S. Cl. ........................................... 514/54; 514/62
(58) Field of Search ...................................... 514/54, 62

(56) References Cited

PUBLICATIONS

Bucci, Luke R.; Role of Nutrition in Healing and Recovery from Acute Injuries, Chronic Injuries, Skin and Surgical Wounds, and Bone Healing, Pennsylvania Chiropractic Association; Feb. 22–23, 1992.*

* cited by examiner

*Primary Examiner*—Theodore J. Criares

(57) ABSTRACT

A therapeutic composition for the protection, treatment and repair of connective tissue in mammals and a method for the treatment of connective tissue in mammals by the administration of the composition. The composition includes glucosamine and preferably chondroitin sulfate. The composition further includes manganese ascorbate which catalyzes the production of collagen and proteoglycans from the glucosamine and the chondroitin sulfate.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–18 are now disclaimed.

\* \* \* \* \*